United States Patent
Boyle et al.

(10) Patent No.: US 6,695,865 B2
(45) Date of Patent: *Feb. 24, 2004

(54) EMBOLIC PROTECTION DEVICE

(75) Inventors: Christopher T. Boyle, San Antonio, TX (US); Steven R. Bailey, San Antonio, TX (US)

(73) Assignee: Advanced Bio Prosthetic Surfaces, Ltd., San Antonio, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/136,246

(22) Filed: Apr. 29, 2002

(65) Prior Publication Data

US 2002/0165576 A1 Nov. 7, 2002

Related U.S. Application Data

(63) Continuation-in-part of application No. 09/532,164, filed on Mar. 20, 2000, now abandoned.
(60) Provisional application No. 60/313,294, filed on Aug. 17, 2001.

(51) Int. Cl.⁷ .............................................. A61M 29/00
(52) U.S. Cl. ...................................................... 606/200
(58) Field of Search ................................ 606/200, 114, 606/113, 127, 159

(56) References Cited

U.S. PATENT DOCUMENTS

| | | |
|---|---|---|
| 4,510,182 A | 4/1985 | Cornils et al. |
| 4,751,099 A | 6/1988 | Niino et al. |
| 4,846,834 A | 7/1989 | von Recum et al. |
| 5,049,251 A | 9/1991 | Inone |
| 5,061,914 A | 10/1991 | Busch et al. |

(List continued on next page.)

FOREIGN PATENT DOCUMENTS

| | | |
|---|---|---|
| DE | 1452370 | 3/1969 |
| EP | 0400947 | 12/1990 |

(List continued on next page.)

OTHER PUBLICATIONS

M. Kohl et al., "Thin film shape memory microvalves with adjustable operation temperature," *Sensors and Actuators*, 83(1–3):214–219 (May 2000).

(List continued on next page.)

*Primary Examiner*—Kevin T. Truong
(74) *Attorney, Agent, or Firm*—Akin Gump Strauss Hauer & Feld, LLP; David G. Rosenbaum (57) ABSTRACT

An embolic protection device includes a catheter body having a central longitudinal lumen, a guidewire positioned within the central longitudinal lumen, and a graft member that is generally tubular in shape in an undeployed state and generally frustroconical in shape in a deployed state. A plurality of openings are formed in the graft member and a plurality of arm members interconnect a proximal end of the graft member with the catheter body. A distal end of the graft member is connected to the guidewire or the atraumatic tip. The graft member may be fabricated of superelastic materials, plastically deformable materials or self-expanding materials and the plurality of openings are capable of diametric expansion and reduction proportionate to the degree of diametric expansion and reduction of a corresponding transverse cross-sectional region of the graft member when in the deployed state to capture emboli or particulate matter and minimize extrusion of the captured material through the openings in the graft member when the graft member is collapsed.

31 Claims, 5 Drawing Sheets

U.S. PATENT DOCUMENTS

| | | |
|---|---|---|
| 5,084,151 A | 1/1992 | Vallana |
| 5,133,845 A | 7/1992 | Vallana et al. |
| 5,158,750 A | 10/1992 | Finicie |
| 5,242,710 A | 9/1993 | Claar et al. |
| 5,277,933 A | 1/1994 | Claar et al. |
| 5,329,514 A | 7/1994 | Eguchi et al. |
| 5,370,684 A | 12/1994 | Vallana et al. |
| 5,376,463 A | 12/1994 | Bak et al. |
| 5,387,247 A | 2/1995 | Vallana et al. |
| 5,421,955 A | 6/1995 | Lau et al. |
| 5,477,864 A | 12/1995 | Davidson |
| 5,514,154 A | 5/1996 | Lau et al. |
| 5,540,820 A | 7/1996 | Terakado et al. |
| 5,545,210 A | 8/1996 | Hess et al. |
| 5,569,295 A | 10/1996 | Lam |
| 5,593,442 A | 1/1997 | Klein |
| 5,603,721 A | 2/1997 | Lau et al. |
| 5,605,714 A | 2/1997 | Dearnaley et al. |
| 5,607,445 A | 3/1997 | Summers |
| 5,607,463 A | 3/1997 | Schwartz et al. |
| 5,609,629 A | 3/1997 | Fearnot et al. |
| 5,628,788 A | 5/1997 | Pinchuk |
| 5,630,840 A | 5/1997 | Mayer |
| 5,647,858 A | 7/1997 | Davidson |
| 5,649,951 A | 7/1997 | Davidson |
| 5,656,036 A | 8/1997 | Palmaz |
| 5,683,453 A | 11/1997 | Palmaz |
| 5,685,961 A | 11/1997 | Pourrezaei et al. |
| 5,690,670 A | 11/1997 | Davidson |
| 5,723,219 A | 3/1998 | Kolluri |
| 5,725,573 A | 3/1998 | Dearnaley et al. |
| 5,728,158 A | 3/1998 | Lau et al. |
| 5,735,896 A | 4/1998 | Amon et al. |
| 5,744,515 A | 4/1998 | Clapper |
| 5,765,418 A | 6/1998 | Rosenberg |
| 5,769,816 A | 6/1998 | Barbut et al. |
| 5,772,864 A | 6/1998 | Moller et al. |
| 5,776,161 A | 7/1998 | Globerman |
| 5,780,807 A | 7/1998 | Saunders |
| 5,782,908 A | 7/1998 | Cahalan et al. |
| 5,782,910 A | 7/1998 | Davidson |
| 5,788,558 A | 8/1998 | Klein |
| 5,798,042 A | 8/1998 | Chu et al. |
| 5,811,151 A | 9/1998 | Hendriks et al. |
| 5,824,045 A | 10/1998 | Alt |
| 5,824,049 A | 10/1998 | Ragheb |
| 5,824,056 A | 10/1998 | Rosenberg |
| 5,840,009 A | 11/1998 | Fischell et al. |
| 5,843,117 A | 12/1998 | Alt et al. |
| 5,843,289 A | 12/1998 | Lee et al. |
| 5,849,206 A | 12/1998 | Amon et al. |
| 5,855,600 A | 1/1999 | Alt |
| 5,855,802 A | 1/1999 | Acciai et al. |
| 5,855,955 A | 1/1999 | Claar et al. |
| 5,858,556 A | 1/1999 | Eckert et al. |
| 5,866,113 A | 2/1999 | Hendriks et al. |
| 5,868,782 A | 2/1999 | Frantzen |
| 5,873,904 A | 2/1999 | Ragheb et al. |
| 5,876,432 A | 3/1999 | Lau et al. |
| 5,879,370 A | 3/1999 | Fischell et al. |
| 5,891,507 A | 4/1999 | Jayaraman |
| 5,895,406 A | 4/1999 | Gray et al. |
| 5,899,935 A | 5/1999 | Ding |
| 5,907,893 A | 6/1999 | Zadno-Azizi |
| 5,910,154 A * | 6/1999 | Tsugita et al. ............... 606/200 |
| 5,911,734 A | 6/1999 | Tsugita et al. |
| 5,913,896 A | 6/1999 | Boyle et al. |
| 5,919,225 A | 7/1999 | Lau et al. |
| 5,925,063 A | 7/1999 | Khosravi |
| 5,928,260 A * | 7/1999 | Chin et al. ................... 606/200 |
| 5,932,299 A | 8/1999 | Katoot |
| 5,938,682 A | 8/1999 | Hojeibane et al. |
| 5,938,697 A | 8/1999 | Killion et al. |
| 5,941,869 A | 8/1999 | Patterson et al. |
| 5,945,153 A | 8/1999 | Dearnaley |
| 5,951,881 A | 9/1999 | Rogers et al. |
| 5,955,588 A | 9/1999 | Tsang et al. |
| 5,962,138 A | 10/1999 | Kolluri et al. |
| 5,968,091 A | 10/1999 | Pinchuk et al. |
| 5,972,018 A | 10/1999 | Israel et al. |
| 5,972,027 A | 10/1999 | Johnson |
| 5,984,905 A | 11/1999 | Dearnaley et al. |
| 5,989,281 A | 11/1999 | Barbut et al. |
| 6,013,855 A | 1/2000 | McPherson et al. |
| 6,015,429 A | 1/2000 | Lau et al. |
| 6,019,784 A | 2/2000 | Hines |
| 6,022,370 A | 2/2000 | Tower |
| 6,027,520 A | 2/2000 | Tsugita et al. |
| 6,027,526 A | 2/2000 | Limon et al. |
| 6,033,433 A | 3/2000 | Ehr et al. |
| 6,042,597 A | 3/2000 | Kveen et al. |
| 6,056,776 A | 5/2000 | Lau et al. |
| 6,059,808 A | 5/2000 | Boussignac |
| 6,066,167 A | 5/2000 | Lau et al. |
| 6,066,168 A | 5/2000 | Lau et al. |
| 6,066,169 A | 5/2000 | McGuinness |
| 6,071,305 A | 6/2000 | Brown et al. |
| 6,086,773 A | 7/2000 | Dufresne et al. |
| 6,096,175 A | 8/2000 | Roth |
| 6,106,642 A | 8/2000 | DiCarlo et al. |
| 6,142,987 A | 11/2000 | Tsugita |
| 6,152,946 A | 11/2000 | Broome et al. |
| 6,165,200 A | 12/2000 | Tsugita et al. |
| 6,168,604 B1 | 1/2001 | Cano |
| 6,171,328 B1 | 1/2001 | Addis |
| 6,277,139 B1 * | 8/2001 | Levinson et al. ........... 606/200 |
| 6,312,463 B1 | 11/2001 | Rourke et al. |
| 6,605,111 B2 | 8/2003 | Bose et al. |
| 2001/0012951 A1 | 8/2001 | Bates et al. |
| 2001/0039449 A1 | 11/2001 | Johnson et al. |

FOREIGN PATENT DOCUMENTS

| | | |
|---|---|---|
| EP | 0442303 | 8/1991 |
| JP | 51055724 | 5/1976 |
| JP | 60162761 | 8/1985 |
| JP | 61-88135 | 7/1994 |
| JP | 11267462 | 10/1999 |
| WO | WO 97/07257 | 2/1997 |
| WO | WO 97/44692 | 11/1997 |
| WO | WO 98/13537 | 4/1998 |
| WO | WO 98/34673 A1 | 8/1998 |
| WO | WO 98/45506 | 10/1998 |
| WO | WO 98/50103 A1 | 11/1998 |
| WO | WO 99/23977 | 5/1999 |
| WO | WO 01/35858 A1 | 5/2001 |
| WO | WO 01/49208 A1 | 7/2001 |
| WO | WO 01/49215 A2 | 7/2001 |
| WO | WO 01/52768 A1 | 7/2001 |
| WO | WO 01/53559 | 7/2001 |
| WO | WO 01/55473 | 8/2001 |
| WO | WO 01/56502 | 8/2001 |

OTHER PUBLICATIONS

Gordon et al., "Liquid Sources for Chemical Vapor Deposition of Group 6 Metals and Metal Nitrides," www.techtransfer.harvard.edu/cgi–bin/TALSearch.cgi?full_report=1&case=3, Case No. 1709.

Curtis et al., "Reactions of Biological Cells to Nanostructures," AVS 46th International Symposium, Paper BI–WeM2 (Oct. 27, 1999).

"Fabrication of Small–Scale Coils and Bands as Photomasks on Optical Fibers for Generation of In–Fiber Gratings, Electromagnets as Micro–NMR Coils, Microtransformers, and Intra–Vascular Stents," www.techtransfer.harvard.edu/cgi–bin/TALSearch.cgi?full_report=1&case=72, Case No. 1263.

"Biocompatibility of Cardiac Cells on Silane–Modified Surfaces," AVS 46th International Symposium, Paper BI–WeM5 (Oct. 27, 1999).

"Biofunctionalization of Surfaces with Peptide Amphilphiles," AVS 46th International Symposium, Paper No. BI–WeM7 (Oct. 27, 1999).

"Plasma Copolymer Surfaces for Cell Culture," AVS 46th International Symposium, Paper No. BI–WeM9 (Oct. 27, 1999).

"Plasma Co–polymer Surfaces for the Conrolled Adsorption of Common Proteins," AVS 46th International Symposium, Paper No. BI–FrM2 (Oct. 29, 1999).

"Biofilm—Titanium Chemistry of Adhesion Using X–ray Photoelectron Spectroscopy," AVS 46th International Symposium, Paper No. BI–FrM10 (Date Missing).

"Nanoscale Patterning of Gold for Attachment of Supported Lipid Bilayers," AVS 46th International Symposium, Paper No. BI–FrM10 (Date Missing).

"Focused Ion Beam NonaFabrication," http://www.glue.umd.edu/~astan/avs04.htm.

"Amorphous Carbon and C:N Thin Films," http://www.glue.umd.edu/~astan/avs01.htm.

"Multilayer Ceramic/Metallic Coatings by Ion Beam–Assisted, Electron Beam Physical Vapor (EB–PVD) Deposition," Penn State Applied Research Laboratory, pp. 1–4 (1997).

"Benefits From Diamond–Like Coated Stainless Steel Stents," http://www.phytis.com/stents0.htm, pp. 1–2.

"Adhesion of Bovine Serus Albumin on Coated DLC (Diamond–Like) and Uncoated ($SiO_2$/$TiO_2$) Sensor Chips," http://www.phytis.com/stent4.htm, pp. 1–2.

"Flow Cytometric Investigation," http://www.phytis.com/stent6.htm, pp. 1–3.

"Pre–clinical and Clinical Evaluation," http://www.phytis.com/stent2.htm, pp. 1–2.

"The New Phytis Stent," http://www.phytis.com/stent1.htm, pp. 1–2.

"Invulnerability and Resistance of DLC–Coating," http://www.phytis.com/stent3.htm, pp. 1–3.

"Material in Use and Its Biocompatibility," http://www.phytis.com/stent5.htm, pp. 1–2.

"Expertise Concerning the Implementation of the Phytis Diamond As Stent Performed at the Institute for Experimental Medicine (IEM)," http://www.phytis.com/stent9.htm. p. 1.

"Phytis L.D.A. Home Page Information," http://www.phytis.com/content/htm, pp. 1–15.

"Risk Analysis of Stents With a Diamond–Like Coated Surface For Use in Prosthetic Implants," http://www.phytis.com/risk.htm, pp. 1–6.

"Directions for Use, Diamond AS® Stent," http://www.phytis.com/direcuse.htm, pp. 1–8.

"Stents: Literature," http://www.phytis.com/liter.htm, pp. 1–8.

"Vacuum Conditions for Sputtering Thin Film TiNi," *Journal of Vacuum Science and Technology, JVST A Online*, pp. 1–2 (Abstract view).

Gisser et al., "Oriented nickel–tetanium shape memory alloy films prepared by annealing during deposition," *Applied Physics Letters*, 61(14):1632–1634 (Abstract view) (Date Missing).

K.S. Fancey et al., "Relative importance of bombardment energy and intensity in ion plating," *Journal of Vacuum Science & Technology A: Vacuum, Surfaces and Films*, 13(2):428–435 (Abstract view) (Mar. 1995).

"Directions for Use, Diamond AS® Stent," http://www.phytis.com/direcuse.htm, pp. 1–8.

"Stents: Literature," http://www.phytis.com/liter.htm, pp. 1–8.

"Vacuum Conditions for Sputtering Thin Film TiNi," *Journal of Vacuum Science and Technology, JVST A Online*, pp. 1–2 (Abstract view).

Gisser et al., "Oriented nickel–tetanium shape memory alloy films prepared by annealing during deposition," *Applied Physics Letters*, 61(14):1632–1634 (Abstract view) (Date Missing).

K.S. Fancey et al., "Relative importance of bombardment energy and intensity in ion plating," *Journal of Vacuum Science & Technology A: Vacuum, Surfaces and Films*, 13(2):428–435 (Abstract view) (Mar. 1995).

F. Goldberg et al., "The Effects of Ion Irradiation on NiTi Shape Memory Alloy Thin Films," *Proceedings of the Second International Conference on Shape Memory and Superelastic Technologies Asilomar Conference Center, Pacific Grove, California, USA*, pp. 177–182 (1997).

L. Buchaillot et al., "Constitutive Parts of a Shape Memory Alloy Titanium Nickel Thin Film Catheter," *Proceedings of the Second International Conference on Shape Memory and Superelastic Technologies Asilomar Conference Center, Pacific Grove, California, USA*, pp. 183–188 (1997).

Q. Pingshan et al., "The Effect of HCD Technological Factors on the NiTi SMA Film Thickness," *Proceedings of the Second International Conference on Shape Memory and Superelastic Technologies Asilomar Conference Center, Pacific Grove, California, USA*, pp. 173–176 (1997).

H. Weixin et al., "The Characteristics of NiTi HCD–Deposited SMA Films," *Proceedings of the Second International Conference on Shape Memory and Superelastic Technologies Asilomar Conference Center, Pacific Grove, California, USA*, pp. 167–172 (1997).

A. Ishida et al., "Microstructure of Ti–Rich TiNi Thin Films," *Proceedings of the Second International Conference on Shape Memory and Superelastic Technologies Asilomar Conference Center, Pacific Grove, California, USA*, pp. 161–166 (1997).

"Thin Film Shape Memory Alloy Microactuators," by TiNi Alloy Company (online).

Johnson et al., "Progress in Thin Film Shape Memory Microactuators," www.sma–mems.com/recent.htm (Overview), pp. 1–5.

W. Ensinger, "The influence of ion irradiation during film growth on the chemical stability of film/substrate systems," *Surface and Coatings Technology*, 80:35–48 (1996).

"Sputtering Targets High–Quality Thin Film Materials," by AMETEK Specialty Metal Products online at www.ametek84.com/fd–sputtering.html, pp. 1–3.

D. Mattox, "A Concise History of Vacuum Coating Technology, Part 2: 1940 to 1975," www.svc.org/HistoryofVac2.html, pp. 1–15.

M. Mrksich, "Model Surfaces for Studying and Controlling the Adhesion of Cells," AVS 47$^{th}$ International Symposium, Invited Paper No. BI+EL–TuA1 (Oct. 3, 2000).

D.S. Sutherland et al., "Cell Response to Chemically and Topographically Modified Surfaces," AVS 47$^{th}$ International Symposium, Paper No. BI+EL–TuA3 (Oct. 3, 2000).

T. Nishikawa et al., "Tissue Formation of Hepatocyles on Micro–Porous Films of Polylactide," AVS 47$^{th}$ International Symposium, Paper No. BI+EL–TuA10 (Oct. 3, 2000).

R. Daw et al., "Endothelial Cell Organization on Micropatterned Protein Surfaces," AVS 47$^{th}$ International Symposium, Paper No. BI–WeP21 (Oct. 4, 2000).

J.E. Houston, "The Nanomechanical Properties of Thin Films," AVS 47$^{th}$ International Symposium, Paper No. TF–TuA1 (Oct. 3, 2000).

E. Kusano et al., "Anomalous Plastic and Elastic Behaviours of Sputter–deposited TiN with 10 or 20 Inserted Thin Al Layers Evaluated by Nanoindentation," AVS 47$^{th}$ International Symposium, Paper No. TF–TuA3 (Oct. 3, 2000).

A.D. Johnson et al., "Recent Progress in the Application of Thin Film Shape Memory Alloys," *Proceedings of the First International Conference on Shape Memory and Superelastic Technologies Asilomar Conference Center, Pacific Grove, California, USA*, pp. 299–310 (1994).

J.D. Busch et al., "Shape Memory Properties in NiTi Sputter–deposited Film," *J Appl. Phys.*, 68(12):6224–6226 (Dec. 15, 1990).

J.A. Waker et al., "Thin–film Processing of TiNi Shape Memory Alloy," *Sensors and Actuators*, A21–A23, pp. 243–246 (1990).

E. Quandt et al., "Sputter–deposition of TiNi, TiNiPd and TiPd films displaying the two–way shape–memory effect," *Sensors and Actuators*, A 53, pp. 434–439 (1996).

V.V. Martynov, "Applications of Shape–Memory Alloy Thin Films," *Proceedings of the Second International Conference on Shape Memory and Superelastic Technologies Asilomar Conference Center, Pacific Grove, California, USA*, pp. 1–8 (1997); and.

"Multicomponent Film Deposition by Target Biasing," *IBM Technical Disclosure Bulletin*, pp. 1–2 (Jul. 1980).

* cited by examiner

EMBOLIC PROTECTION DEVICE

CROSS-REFERENCE TO RELATED APPLICATIONS

This application is a Continuation-in-Part of U.S. patent application Ser. No. 09/532,164 filed on Mar. 20, 2000, now abandoned the disclosure of which is hereby incorporated by reference. This application also claims the benefit of U.S. Provisional Application No. 60/313,294 filed on Aug. 17, 2001.

BACKGROUND OF THE INVENTION

The present invention relates generally to embolic protection devices. More specifically, the present invention pertains to catheter-based devices for trapping emboli, tissue, arterioschlerotic plaque or other particulate matter in the bloodstream. During angioplasty and stent implantation procedures, oftentimes emboli or other particulate matter is dislodged from the vascular wall. Once dislodged, this particulate matter enters the bloodflow and, unless trapped, collected and removed from the body in some fashion, poses a serious risk to the patient.

Conventional embolic protection devices typically employ umbrella-like baskets in which structural support members are fabricated of elastically strained segments, such as stainless steel or nitinol wire or hypotubing, and rely upon the relative antegrade and retrograde movement of coaxial shafts of a catheter member to deploy and collapse the embolic basket in a manner similar to the way an umbrella is opened and closed. One disadvantage of these umbrella-like devices is increased profile because the material forming the embolic basket must be folded in some manner when the basket is not deployed. Another disadvantage of umbrella-like devices is the excess flap material comprising the embolic basket when under-deployed will fold and invaginate into the lumen of the vessel causing poor apposition between the vessel wall and embolic basket.

Moreover, conventional embolic protection devices are typically fashioned of materials having a relatively constant open surface area across the surface area of the embolic basket. The structure of the embolic basket in conventional embolic protection devices is such that the open spaces are dimensioned to capture emboli or other particulate matter of a certain size that are dislodged as a result, for example, of the angioplasty or stent implantation procedure. With conventional embolic protection devices, the design of the device anticipates that a certain fraction of emboli or particulate matter will pass through the device and into the patient's general circulation.

BRIEF SUMMARY OF THE INVENTION

In accordance with one aspect of the invention, an embolic protection device comprising a first elongate member having a lumen, a second elongate member extending through the lumen and being movable with respect to the first elongate member, a graft member having a proximal end portion connected to the first elongate member and a distal end portion connected to the second elongate member, and a plurality of openings extending through the graft member along a length thereof is provided. The graft member is expandable from an undeployed generally tubular state to a deployed generally frustroconical state upon relative movement between the first and second elongate members in a first direction. The openings generally decrease in size from the proximal end toward the distal end when the graft member is in the deployed state to thereby capture and retain emboli and other particulate matter of different sizes.

In accordance with a further aspect of the invention, an embolic protection device comprises a catheter body having a central longitudinal lumen, a guidewire having an atraumatic tip positioned at a distal end thereof, and a graft member movable between an undeployed state and a deployed state. The guidewire is coaxially positioned within the central longitudinal lumen of the catheter body. The graft member is preferably of a generally tubular shape in the undeployed state and of a generally frustroconical shape in the deployed state. The graft member has a plurality of openings that extend along a length thereof. A plurality of arm members interconnect a proximal end of the graft member and the catheter body. A distal end of the graft member is connected to one of the guidewire and the atraumatic tip. The graft member is movable between the undeployed and deployed states upon relative movement between the catheter body and the guide wire. Preferably, the graft member is constructed of a material such that each opening expands or reduces in size in proportion to an amount of radial expansion or reduction, respectively, of a corresponding transverse cross sectional region of the graft member with which the opening is associated, to thereby capture emboli and other particulate matter when the graft member is in the deployed state and minimize extrusion of the captured material through the openings in the graft member when the graft member is in the undeployed state.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

It is noted that the drawings are intended to represent only typical embodiments of the invention and therefore should not be construed as limiting the scope thereof. The invention will now be described in greater detail with reference to the drawings, wherein like parts throughout the drawing figures are represented by like numerals.

DETAILED DESCRIPTION OF THE INVENTION

Turning now to the drawings, and with particular reference to FIGS. 1–4, an embolic protection device (EPD) 10 in accordance with the present invention is illustrated. The EPD 10 is especially applicable as an in-dwelling device or for use in conjunction with an interventional device, such as a PTCA balloon catheter, for capturing emboli and/or other particulate matter within the bloodstream of a patient. The EPD 10 serves at least the dual purpose of: 1) functioning as a standard guide wire thereby allowing a catheter-borne medical device, such as a balloon dilation catheter of the type typically used for angioplasty and balloon expandable stent deployment, to be delivered to a site within a body cavity; and 2) removing particulate matter from the bloodstream that may be associated with the interventional procedure that requires use of the guide wire.

Figures 1, 2:
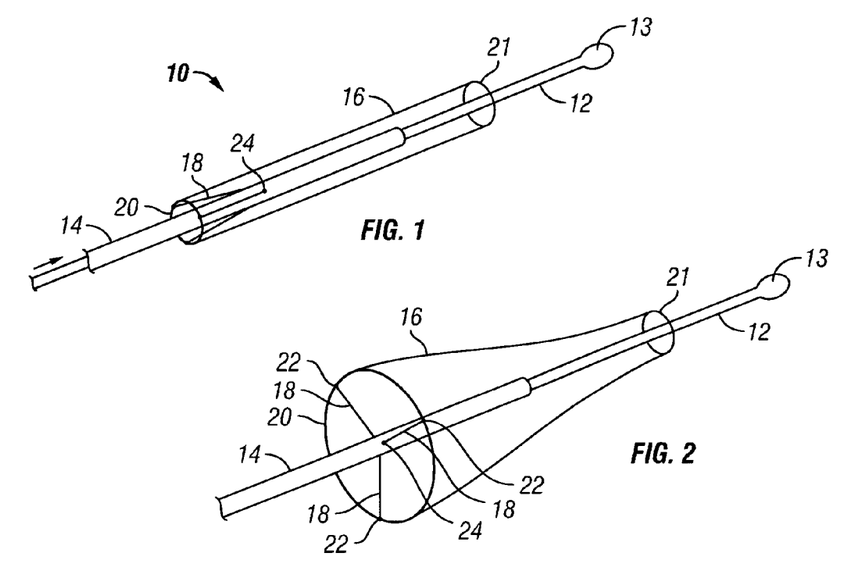
FIG. 1 is a perspective view of a first embodiment of the inventive embolic protection device.
FIG. 2 is a perspective view of the first embodiment of the inventive embolic protection device in its deployed state.

The EPD 10 preferably comprises a guidewire 12 terminated at a distal end thereof with an atraumatic tip 13, a tubular catheter body 14 coaxially and concentrically positioned about the guidewire 12 and reciprocally moveable thereupon, and a graft member or embolic basket 16 coaxially and concentrically positioned about the tubular catheter body 14 and the guidewire 12. The guidewire 12 may be tubular or solid along its entire length or may transition between solid and tubular along its length. A distal end 21 of the graft member 16 is coupled to the guidewire 12 proximal to the atraumatic tip 13 and distal to the catheter body 14. A proximal end 20 of the graft member 16 is coupled to the tubular catheter body 14 by a plurality of articulating arm members 18. The articulating arm members 18 may be constructed of braided wire.

In accordance with a preferred embodiment of the invention, the graft member 16 is fabricated of a metal, pseudometallic or polymeric film and formed either as a tubular member or as a planar member then rolled into a tubular shape. Each of the plurality of articulating arm members 18 are coupled at a first end 22 thereof to the proximal end 20 of the graft member 16 and at a second end 24 thereof to a distal region of the tubular catheter body 14.

The graft member 16 has a plurality of openings 30 that pass through a wall of the graft member 16 and communicate between an abluminal wall surface and a luminal wall surface of the graft member 16 to thereby form a porous thin-walled polymer or metallic tube. The plurality of openings 30 permit passage of body fluid, such as blood, through the graft member 16, but exclude the passage of emboli and other particulate matter when the graft member 16 is diametrically enlarged.

In accordance with a preferred embodiment of the invention, the plurality of openings 30 generally comprise a plurality of longitudinal slots formed in the graft member 16 which enlarge and open when the graft member 16 is expanded to its enlarged diameter. While it is expressly contemplated that the openings 30 may be formed as longitudinal slots in the graft member 16, those skilled in the art will appreciate that other opening geometries, such as circles, ovals, ellipses, squares, diamonds, star-shapes, polygons or the like may also be employed. Additionally, not only the geometry of the plurality of openings 30, but the sizes of the openings may be varied. By varying the size of the openings along the longitudinal axis of the graft member 16, it is possible to achieve greater control over the relative porosity of the graft member 16 along its longitudinal axis when in the expanded state in order to capture emboli and other particulate matter in the blood stream.

The particular material used to form the graft member 16 is chosen for its biocompatibility, mechanical properties, i.e., tensile strength, yield strength, and, in the case where vapor deposition is employed to fabricate the graft member 16, its ease of deposition. By way of example, the graft member 16 can be constructed of a porous thin-walled polymer or metallic tube that is capable of being elastically or superelastically expanded diametrically such as to take on a generally frustroconical shape in its deployed state under the influence of a positive pressure such as that imparted by the plurality of articulating arm members.

For purposes of this application, the terms "pseudometal" and "pseudometallic" are intended to mean a biocompatible material which exhibits biological response and material characteristics substantially the same as biocompatible metals. Examples of pseudometallic materials include, for example, composite materials and ceramics. Composite materials are composed of a matrix material reinforced with any of a variety of fibers made from ceramics, metals, or polymers. The reinforcing fibers are the primary load carriers of the material, with the matrix component transferring the load from fiber to fiber. Reinforcement of the matrix material may be achieved in a variety of ways. Fibers may be either continuous or discontinuous. Reinforcement may also be in the form of particles. Examples of composite materials include those made of carbon fibers, boron fibers, boron carbide fibers, carbon and graphite fibers, silicon carbide fibers, steel fibers, tungsten fibers, graphite/copper fibers, titanium and silicon carbide/titanium fibers.

The graft member 16 may be fabricated of pre-existing conventional wrought materials, such as stainless steel or nitinol hypotubes, or may be fabricated by thin film techniques. In addition to wrought materials that are made of a single metal or metal alloy, the inventive grafts may comprise a monolayer of biocompatible material or of a plurality of layers of biocompatible materials. Laminate structures are generally known to increase the mechanical strength of sheet materials, such as wood or paper products. Laminates are used in the field of thin film fabrication also to increase the mechanical properties of the thin film, specifically hardness and toughness. Laminate metal foils have not been used or developed because the standard metal forming technologies, such as rolling and extrusion, for example, do not readily lend themselves to producing laminate structures. Vacuum deposition technologies can be developed to yield laminate metal structures with improved mechanical properties. In addition, laminate structures can be designed to provide special qualities by including layers that have special properties such as superelasticity, shape memory, radio-opacity, corrosion resistance etc.

The metals contemplated include, without limitation, the following: titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel. Additionally, in the case where multiple layers and/or laminates of films are employed, each layer of material used to form the graft may be doped with another material for improving properties of the material, such as radio-opacity or radioactivity, for example by doping with tantalum, gold, or radioactive isotopes.

When the EPD 10 is in its undeployed or collapsed state, as depicted in FIG. 1, each of the plurality of articulating arm members 18 is positioned parallel to a longitudinal axis of the EPD 10. When relative movement between the guidewire 12 and the catheter body member 14 occurs, such as by antegrade movement of the guidewire 12 or retrograde movement of the catheter body member 14, each of the articulating arm members 18 are urged from their longitudinal orientation into a generally radial orientation relative to the longitudinal axis of the EPD 10.

Figure 3A:
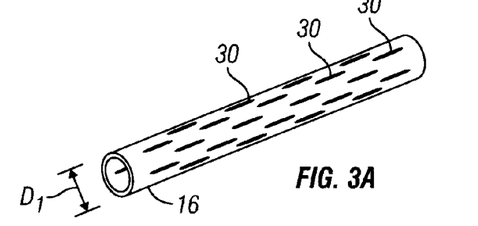
FIG. 3A is a diagrammatic perspective view of a graft portion of the inventive embolic protection device in its collapsed or undeployed state.
Figure 3B:
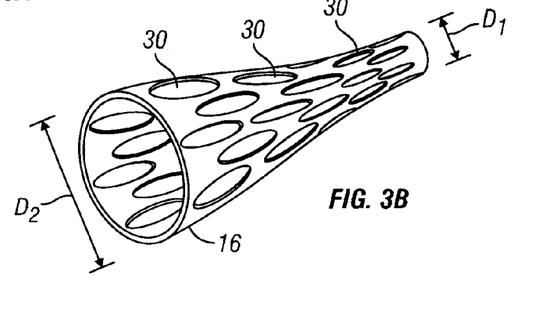
FIG. 3B is a diagrammatic perspective view of the graft portion in its expanded or deployed state.

As each of the articulating arm members 18 undergo their orientational change, a positive pressure is exerted by the plurality of articulating arm members 18 to the proximal end 20 of the graft member 16, which then undergoes a geometric change and diametrically enlarges from its undeployed diameter $D_1$ to its enlarged deployed diameter $D_2$, as depicted in FIGS. 3A and 3B. The diametric change of the graft member 16 from $D_1$ to $D_2$ is preferably an elastic or superelastic deformation in which $D_1$ is associated with the low strain configuration of the graft member 16. However, in the case where $D_2$ is associated with the low strain configuration, release of a constraining force exerted by arms 18 can permit self-expansion of the graft member 16. The diametric change of the graft member 16 from $D_1$ to $D_2$ may also be associated with a plastic deformation.

In one embodiment, the articulating arm members may have a low strain configuration that is associated with the collapsed diameter $D_1$. In this embodiment, a compressive load is applied to the articulating arm members 18 when either the guidewire 12 or the catheter body member 14 are moved relative to one another thus causing the articulating arm members to buckle outward and enlarging the proximal end 20 of the graft member 16 to $D_2$. The articulating arm members 18 and the graft member 16 assume their collapsed configurations upon removal of the compressive load.

In a further embodiment, the articulating arm members 18 may alternatively have a low strain configuration that is associated with the deployed diameter $D_2$. In this embodiment, a tensile load must be maintained in the articulating arm members 18 to keep the articulating arm members 18 and the graft member 16 in the collapsed state $D_1$. The articulating arm members 18 and the graft member 16 assume their respective deployed configurations upon removal of the tensile load when either the guidewire 12 or the catheter body member 14 are moved relative to one another. The articulating arm members 18 and the graft member 16 reassume their respective collapsed configuration upon reapplication of the tensile load.

In accordance with a preferred embodiment of the present invention, the graft member 16 is fabricated of a superelastic material which is capable of undergoing two-way transition between an austenite phase to a martensite phase as a result of stress and strain applied through the plurality of articulating arm members 18 to diametrically expand and diametrically collapse the graft member 16.

Preferably, the distal end 21 of the graft member 16 does not undergo any or any appreciable diametric expansion. However, during diametric expansion of the proximal end 20 of the graft member 16, the graft member 16 assumes a generally frustroconical shape with a taper of the graft member from its proximal end 20 to its distal end 21.

Because the graft member 16 undergoes differential diametric expansion along its longitudinal axis, the relative degree of expansion of the plurality of openings 30 along the longitudinal axis of the graft member 16 will also vary. The openings 30 toward the proximal end 20 of the graft member 16 will exhibit a greater degree of expansion than will the openings 30 toward the distal end 21 of the graft member 16. Thus, in its expanded state, the graft member 16 will have a differential open surface area along its longitudinal axis. With this arrangement, the larger diametric region of the graft member 16 has larger openings in closer proximity to the walls of the blood vessel and the relatively slower region of the fluid flow through the blood vessel, where larger, slower moving emboli and particulate matter is more likely to be located in the blood flow. Conversely, the distal region of the graft member 16 has smaller openings in closer positional proximity to a central luminal region of the blood flow, where there is a relatively faster rate of fluid flow and where the smaller, faster moving, emboli and particulate matter is more likely to be found in the blood flow. The EPD 10, therefore, exposes the blood flow distal an interventional device to a gradient of openings in the graft member 16 which more closely approximates the blood flow velocities relative to the transverse cross-sectional area of the vasculature and positions dimensionally sized openings in a more correct orientation relative to the blood flow velocities than with conventional devices. The expansive feature of the EPD 10 also allows for improved apposition of the graft member 16 to the vessel wall regardless of the expansion ratio $D_2/D_1$, particularly since the graft member 16 is not subject to folding, as in the prior art.

Figure 4:
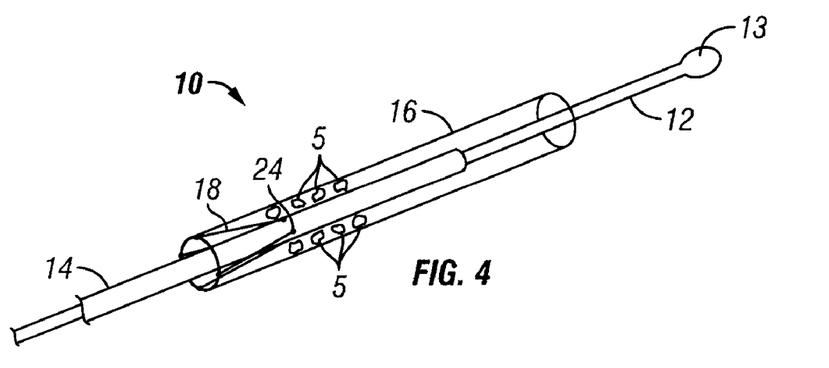
FIG. 4 is a perspective view of the first embodiment of the inventive embolic protection device in its collapsed or undeployed state with captured emboli.

Additionally, relative movement of either the guidewire 12 or the catheter body member 14, depending on the embodiment of the present invention, collapses the graft member 16 with a concomitant reduction in size of the openings 30. As depicted in FIG. 4, any emboli or particulate matter 5 is captured and sequestered within the lumen of the graft member 16. During contraction of the graft member 16, the size of the openings 30 also reduces, which minimizes undesired extrusion of the captured emboli and particulate matter through the openings 30 and ejection of the extrudate into the blood flow of the patient. Thus, a greater quantum of emboli and other particulate matter is both captured and withdrawn from the body with the present invention than is found with conventional embolic protection devices.

FIGS. 5–8 illustrate an embolic protection device 50 in accordance with a further embodiment of the invention. Like the EPD 10, the EPD 50 also generally comprises a graft member 52 fabricated of metal, polymeric or pseudometallic materials as described above, a guidewire 54, and a catheter body member 58. The graft member 52 is preferably fabricated of a mesh material having a woven web 51 and a plurality of interstitial spaces 55 within the woven web 51. The graft member 52 is coaxially and concentrically positioned about the guidewire 54. The catheter body member 58 is also coaxially and concentrically positioned about the guidewire 54. The catheter body member 58 is interconnected with a proximal end 53 of the graft member 52 by a plurality of arms 60. Each of the plurality of arms 60 is preferably oriented parallel to the longitudinal axis of the EPD 50 when the EPD is in its undeployed state. When the EPD 50 is in its undeployed state, a distal end of the catheter body member may be proximally positioned relative to the proximal end of the graft member 52, or it may be concentrically positioned between the graft member 52 and the guidewire 54. A distal end of the graft member 52 is coupled either to the guidewire 54 or to an atraumatic tip 56.

Figure 5:
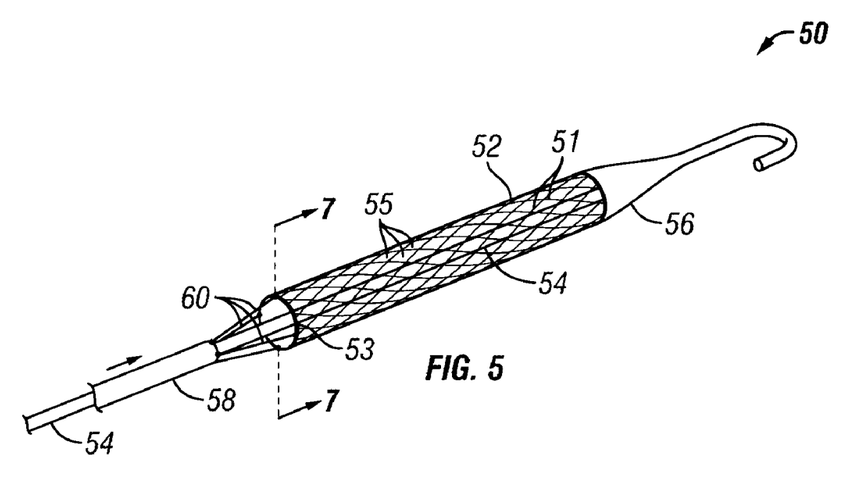
FIG. 5 is a perspective view of a second embodiment of the inventive embolic protection device in its collapsed or undeployed state.
Figure 6:
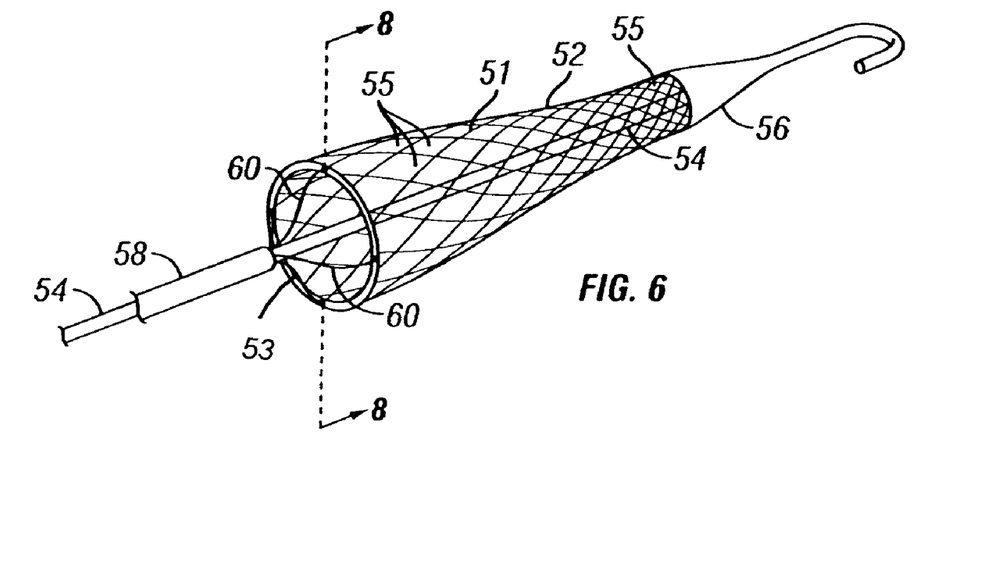
FIG. 6 is a perspective view of the second embodiment of the inventive embolic protection device in its expanded or deployed state.
Figure 7:
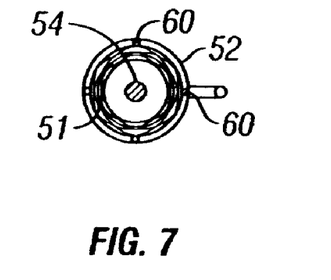
FIG. 7 is a cross-sectional view taken along line 7—7 of FIG. 5.

Relative movement of either the guidewire 54 and atraumatic tip 56 in a retrograde direction or of the catheter body 58 in an antegrade direction, exerts an applied pressure to the plurality of arms 60 causing flexion of the plurality of arms 60 from the longitudinal axis and into a radial orientation, and the arms exert a radially expansive force to the proximal end 53 of the graft member 52.

In another embodiment, relative movement of either the guidewire 54 and atraumatic tip 56 in a retrograde direction or of the catheter body 58 in an antegrade direction reduces or removes a tensile stress present in the articulating arm members 60 such as to allow the articulating arm members 60 to assume a lower strain deployed configuration.

Figure 8:
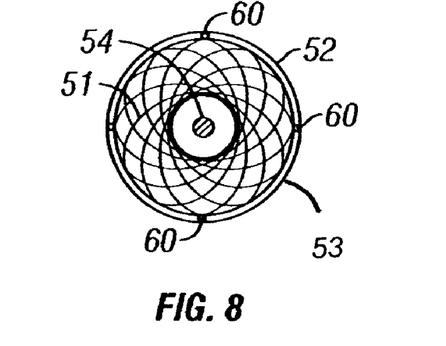
FIG. 8 is a cross-sectional view taken along line 8—8 of FIG. 6.

As depicted in FIGS. 6 and 8, the proximal end 53 of graft member 52 diametrically enlarges and urges the graft member 52 from a tubular shape to a frustroconical shape. Again, like EPD 10, the interstitial openings 55 in EPD 50 also enlarge proportionate to the degree of diametric enlargement of the corresponding transverse cross-sectional area of the graft 52. Again, when the EPD 50 is in its deployed state, there is a differential open surface area along the longitudinal axis of the graft member 52 that presents a gradient in open surface area. Similar to EPD 10, when the graft member 52 is collapsed, the enlarged interstitial openings 55 in web 51 reduce in size to capture emboli and particulate matter within the graft member 52 while minimizing extrudate through the openings 55 during collapse.

Like the EPD 10, the graft member 52 is preferably fabricated of a superelastic material and is capable of undergoing two-way transformation from the austenite to the martensite phase under the influence of an applied stress and strain from relative movement of the guidewire 54 and catheter body 58 through the plurality of arms 60. Each of the plurality of arms 60 may also be fabricated of superelastic material and have both an austenitic phase shape and a martensitic phase shape corresponding to the transformation shapes of the graft member 52. By fabricating both the graft 52 and the plurality of arms 60 of superelastic materials, the relative movement of the guidewire 54 and the catheter body member 58 exerts an applied stress-strain to the arms 60 and graft member 52 sufficient to cause phase transition and, therefore, transforms the geometries of the arms 60 and graft member 52. Alternatively, the graft member 52 and the plurality of arms 60 may be fabricated of like plastically deformable or self-expanding materials, such as stainless steel, or may be fabricated of different materials, with the arms 60 being fabricated of a self-expanding elastically, plastically or superelastically deformable material and the graft member 54 being fabricated of an elastic or superelastic material. Thus, the arms 60 and the graft member 54 may be fabricated of like or different materials that exhibit like or distinct material properties.

Figure 9A:
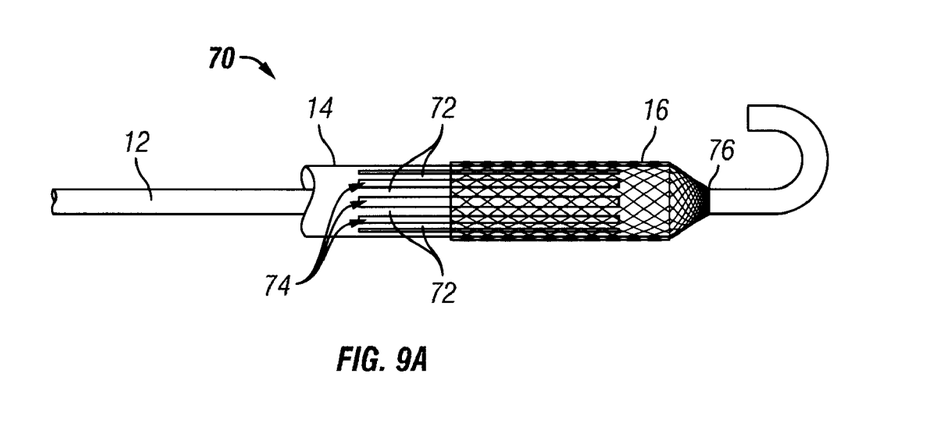
FIG. 9A is a side elevational view of a third embodiment of the inventive embolic protection device in its collapsed or undeployed state.
Figure 9B:
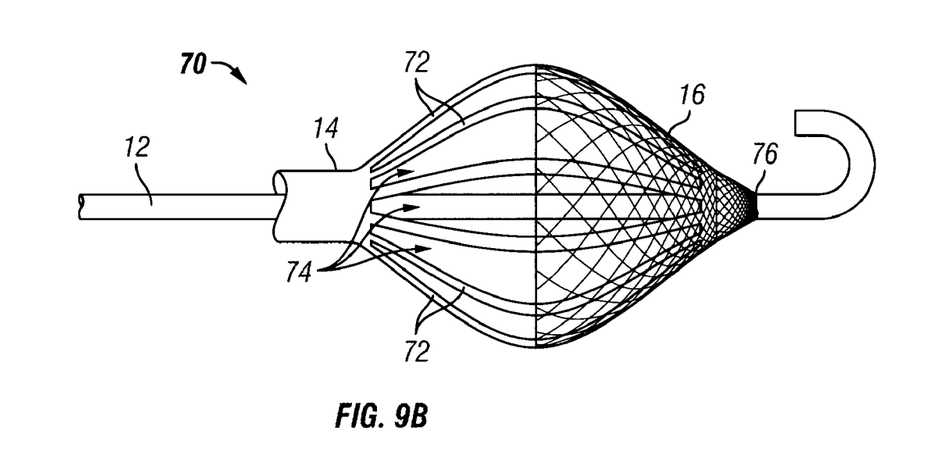
FIG. 9B is a side elevational view of the third embodiment of the inventive embolic protection device in its expanded or deployed state.

FIGS. 9A and 9B illustrate an embolic protection device 70 in accordance with other embodiments of the invention. The EPD 70 is similar in construction to the EPD 10, with the exception that the articulating arm members 18 are replaced by articulating arm members 72 that are integrally formed in a distal portion of the catheter body member 14. The articulating arm members 72 are formed by cutting slits 74 into a distal tubular portion of the catheter body member 14. As shown, the slits extend longitudinally along the catheter body member 14. Alternatively, the slits may spiral around a portion of the catheter body member 14. The graft member 16 is placed concentrically around a distal portion of the catheter body member 14, such that it is over the arm members 72 and slits 74. The catheter body member 14 and the graft member 16 are connected (e.g., by welding) to the guide wire 12 at the distal end of the catheter body member 14 and graft member 16 by connection 76. In the embodiment shown in FIG. 9A, the articulating arm members 72 are shape set in a closed configuration. To deploy the graft member 16, the catheter body member 14 is moved distally while the guide wire 12 is not moved, thereby causing articulating arm members 72 to buckle outward and deploy the graft member 16. In the embodiment shown in FIG. 9B, the articulating arm members 72 may also have a low strain configuration that is associated with the deployed diameter $D_2$ of the graft member 16. The catheter body member 14 is pulled proximally with respect to the guide wire 12 to maintain tension with the guide wire 12 such that the articulating arm members 72 are straightened and the graft member 16 remains in an undeployed ("captured") state. Relieving the tension between the guide wire 12 and the catheter body member 14 by moving the catheter body member 14 distally with respect to the guide wire 12, the arm members 72 return to an open shape such that graft member 16 is deployed.

Figure 10A:
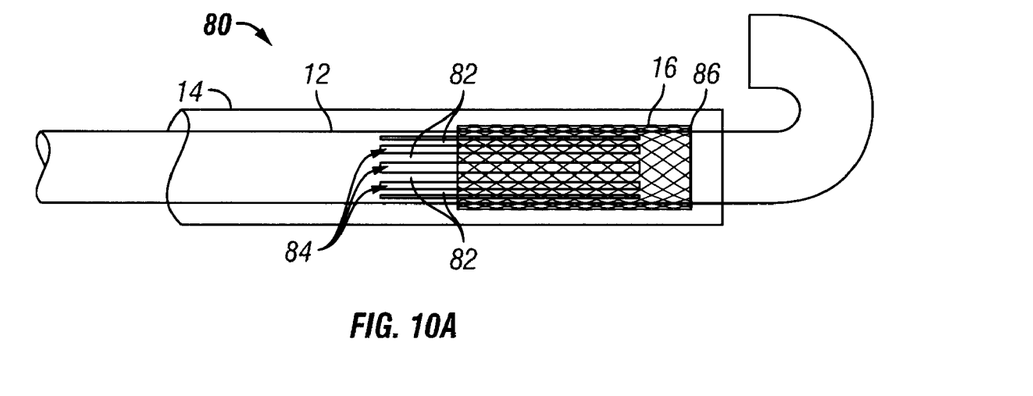
FIG. 10A is a side elevational view of a fourth embodiment of the inventive embolic protection device in its collapsed or undeployed state.
Figure 10B:
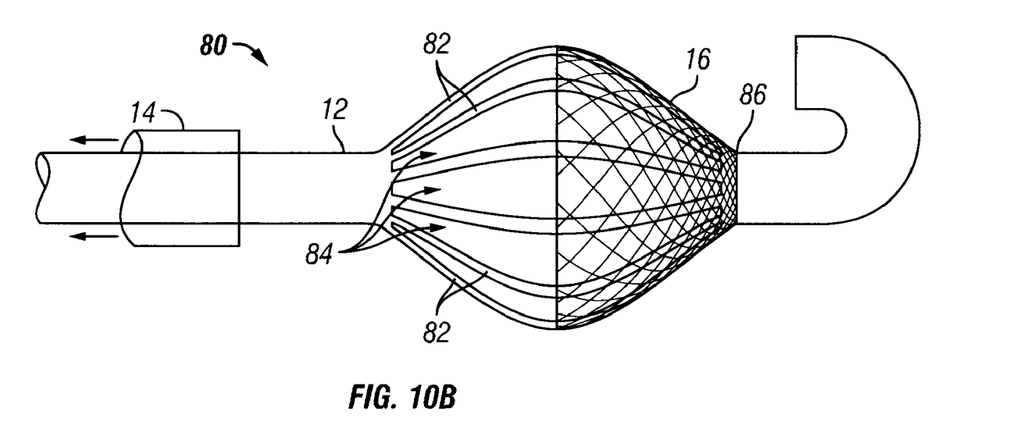
FIG. 10B is a side elevational view of the fourth embodiment of the inventive embolic protection device in its expanded or deployed state.

FIGS. 10A and 10B illustrate an embolic protection device 80 in accordance with another embodiment of the invention. The EPD 80 is similar in construction to the EPD 10, with the exception that the articulating arm members 18 are replaced by articulating arm members 82 that are integrally formed in a distal portion of the guidewire 12. The articulating arm members 82 are formed by cutting slits 84 into a distal tubular portion of the guidewire 12, when at least a portion of the guide wire 12 is of tubular shape. As shown, the slits extend longitudinally along the guide wire 12. Alternatively, the slits may spiral around a portion of the guide wire 12. The graft member 16 is placed concentrically around a distal portion of the guide wire 12, such that it is over the arm members 82 and slits 84 and can be connected (e.g., by welding) to the guide wire 12 at the distal end of the graft member by connection 86. In this embodiment, the articulating arm members 82 may also have a low strain configuration that is associated with the deployed diameter $D_2$ and the catheter body member 14 acts as a capture sheath such that in the captured state, the catheter body member 14 prevents the articulating arm members 82 from expanding the graft member 16. With this arrangement, the catheter body member 14 is retracted for deployment of the articulating arm members 82 which in turn force the graft member into the deployed or expanded condition, as shown in FIG. 10B. Likewise, the catheter body 14 can be moved in the opposite direction to force the articulating arm members 82, and thus the graft member 16, to their collapsed or undeployed condition as shown in FIG. 10A. It will be understood that the articulating arm members can alternatively be in the form of wire like attachments connected to the distal end of the guidewire 12.

Thus, it will be appreciated by those of ordinary skill in the art that the inventive embolic protection device is suitable for use alone as an in-dwelling device or for use in conjunction with a balloon catheter, for capturing emboli and/or other particulate matter within the bloodstream of a patient. Moreover, the embodiments of the inventive embolic protection device employ a porous graft that is urged, either under the influence of superelastic phase transformation, plastic deformation or self-expanding properties, into a frustroconical shape having a proximal end that is diametrically enlarged to capture emboli and other particulate matter, then is collapsible to capture the matter within the graft with a minimal degree of extrusion of particulate matter through the pores of the graft. The porous openings in the graft are differentially expansible proportionate to the degree of expansion of a corresponding transverse cross-sectional region of the graft member, where the porous openings differentially expand and contract during deployment and collapse of the graft to capture the particulate matter therein.

When the inventive embolic protection device is withdrawn from the body, the emboli and particulate matter within the graft member are captured and sequestered. In conventional devices that are characterized by more static open regions, there is a tendency for the emboli and particulate matter to extrude through the open regions when the embolic device is collapsed. Because conventional devices employ more constant area of open region, a greater quantum of emboli and particulate matter will be ejected by extrusion through the open regions. However, with the present invention, the dimension of the open regions changes during diametric expansion and during diametric contraction. Because there is a reduction in the dimension of the open regions during diametric contraction, the present invention is substantially less susceptible to embolic extrusion through the graft member during collapse of the graft member. Thus, a greater quantum of emboli and other particulate matter is both captured and withdrawn from the body with the present invention than is found with conventional embolic protection devices.

EXAMPLE 1

In accordance with the preferred embodiment of fabricating the inventive microporous metallic implantable device in which the device is fabricated from vacuum deposited nitinol tube, a cylindrical deoxygenated copper substrate is provided. The substrate is mechanically polished and/or electropolished to provide a substantially uniform surface topography for accommodating metal deposition thereupon. A cylindrical hollow cathode magnetron sputtering deposition device was employed, in which the cathode was on the outside and the substrate was positioned along the longitudinal axis of the cathode. A cylindrical target consisting either of a nickel-titanium alloy having an atomic ratio of nickel to titanium of about 50–50% and which can be adjusted by spot welding nickel or titanium wires to the target, or a nickel cylinder having a plurality of titanium strips spot welded to the inner surface of the nickel cylinder, or a titanium cylinder having a plurality of nickel strips spot welded to the inner surface of the titanium cylinder is provided. It is known in the sputter deposition acts to cool a target within the deposition chamber by maintaining a thermal contact between the target and a cooling jacket within the cathode. In accordance with the present invention, it has been found useful to reduce the thermal cooling by thermally insulating the target from the cooling jacket within the cathode while still providing electrical contact to it. By insulating the target from the cooling jacket, the target is allowed to become hot within the reaction chamber. Two methods of thermally isolating the cylindrical target from the cooling jacket of the cathode were employed. First, a plurality of wires having a diameter of 0.0381 mm were spot welded around the outer circumference of the target to provide an equivalent spacing between the target and the cathode cooling jacket. Second, a tubular ceramic insulating sleeve was interposed between the outer circumference of the target and the cathode cooling jacket. Further, because the Ni—Ti sputtering yields can be dependant on target temperature, methods which allow the target to become uniformly hot are preferred.

The deposition chamber was evacuated to a pressure less than or about $2$–$5 \times 10^{-7}$ Torr and pre-cleaning of the substrate is conducted under vacuum. During the deposition, substrate temperature is preferably maintained within the range of 300 and 700 degrees Centigrade. It is preferable to apply a negative bias voltage between 0 and $-1000$ volts to the substrate, and preferably between $-50$ and $-150$ volts, which is sufficient to cause energetic species arriving at the surface of the substrate. During deposition, the gas pressure is maintained between 0.1 and 40 mTorr but preferably between 1 and 20 mTorr. Sputtering preferably occurs in the presence of an Argon atmosphere. The argon gas must be of high purity and special pumps may be employed to reduce oxygen partial pressure. Deposition times will vary depending upon the desired thickness of the deposited tubular film. After deposition, the plurality of microperforations are formed in the tube by removing regions of the deposited film by etching, such as chemical etching, ablation, such as by excimer laser or by electric discharge machining (EDM), or the like. After the plurality of microperforations are formed, the formed microporous film is removed from the copper substrate by exposing the substrate and film to a nitric acid bath for a period of time sufficient to remove or dissolve the copper substrate.

While the invention has been taught with specific reference to the above-described embodiments, those skilled in the art will recognize that changes can be made in form and detail without departing from the spirit and the scope of the invention. Thus, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. An embolic protection device, comprising:

a first elongate member having a lumen;

a second elongate member extending through the lumen and being movable with respect to the first elongate member; and a graft member constructed from a metal having a characteristic that is at least one of a superelastic material, a plastically deformable material and an elastic material, the graft member having a proximal end portion connected to the first elongate member and a distal end portion connected to the second elongate member, and a plurality of openings extending through the graft member along a length thereof;

the graft member being expandable from an undeployed generally tubular state to a deployed generally frustroconical state upon relative movement between the first and second elongate members in a first direction, the openings decreasing in size from the proximal end toward the distal end when the graft member is in the deployed state to thereby capture and retain emboli and other particulate matter of different sizes.

2. An embolic protection device according to claim 1, wherein the openings are substantially uniform in size when the graft member is in the undeployed state.

3. An embolic protection device according to claim 1, and further comprising a plurality of arm members extending between the first elongate member and the proximal end of the graft member, such that relative movement of the first and second elongate members in the first direction causes the arm members to move from a generally axial orientation to a generally radial orientation to thereby radially expand the proximal end of the graft member.

4. An embolic protection device according to claim 3, wherein the distal end of the graft member is substantially restrained against radial expansion such that the diameter of the graft member decreases from the proximal end toward the distal end when the graft member is in the deployed state.

5. An embolic protection device according to claim 4, wherein the size of each opening is proportional to the diameter of the graft member at which each opening is located.

6. An embolic protection device according to claim 5, wherein relative movement of the first and second elongate members in a second direction opposite the first direction causes the graft member to return to the undeployed state, thereby reducing the size of the openings at least at the proximal end, such that the emboli and other particulate matter can be entrapped within the graft member.

7. An embolic protection device according to claim 6, wherein the openings are substantially uniform in size when the graft member is in the undeployed state.

8. An embolic protection device according to claim 1, wherein the distal end of the graft member is substantially restrained against radial expansion such that the graft member decreases in diameter from the proximal end toward the distal end when the graft member is in the deployed state.

9. An embolic protection device according to claim 8, wherein the size of each opening is proportional to the diameter of the graft member at which each opening is located.

10. An embolic protection device according to claim 1, wherein relative movement of the first and second elongate members in a second direction opposite the first direction causes the graft member to return to the undeployed state, thereby reducing the size of the openings at least at the proximal end, such that the emboli and other particulate matter can be entrapped within the graft member.

11. An embolic protection device according to claim 1, wherein the graft member is constructed of a thin film metal.

12. An embolic protection device according to claim 11, wherein the thin film metal comprises a nickel titanium alloy.

13. An embolic protection device according to claim 1, wherein the graft member is constructed of braided wire.

14. An embolic protection device according to claim 1, wherein the first elongate member is a catheter.

15. An embolic protection device according to claim 14, wherein the second elongate member is a guide wire.

16. An embolic protection device according to claim 15, wherein the guide wire has an atraumatic tip at a distal end thereof.

17. An embolic protection device according to claim 1, wherein the second elongate member has a tubular distal portion, and further comprising a plurality of arm members integrally formed in the tubular portion in proximity with the proximal end of the graft member, the plurality of arm members being biased toward an expanded arm position and normally restrained in a retracted arm position by the first elongate member, such that relative movement of the first and second elongate members in the first direction causes the arm members to move from the retracted arm position toward the expanded arm position to thereby radially expand the proximal end of the graft member.

18. An embolic protection device comprising:
a catheter body having a central longitudinal lumen;
a guidewire having an atraumatic tip positioned at a distal end thereof, the guidewire being coaxially positioned within the central longitudinal lumen of the catheter body; and
a graft member movable between an undeployed state and a deployed state, the graft member being of a generally tubular shape in the undeployed state and of a generally frustroconical shape in the deployed state, the graft member comprising a plurality of openings extending along a longitudinal axis thereof, the openings decreasing in size from the proximal end toward the distal end when the graft member is in the deployed state, with a distal end of the graft member being connected to one of the guidewire and the atraumatic tip, the graft member being movable between the undeployed and deployed states upon relative movement between the catheter body and the guide wire, the graft member being constructed of a metal having a characteristic that is at least one of a superelastic material, a plastically deformable material and an elastic material such that each opening expands and reduces in size in proportion to an amount of radial expansion and reduction, respectively, of a corresponding transverse cross sectional region of the graft member with which the opening is associated, to thereby capture emboli and other particulate matter when the graft member is in the deployed state and minimize extrusion of the captured material through the openings in the graft member when the graft member is in the undeployed state.

19. An embolic protection device according to claim 18, wherein the openings are substantially uniform in size when the graft member is in the undeployed state.

20. An embolic protection device according to claim 18, wherein the distal end of the graft member is substantially restrained against radial expansion such that the graft member decreases in diameter from the proximal end toward the distal end when the graft member is in the deployed state.

21. An embolic protection device according to claim 18, wherein the graft member is constructed of a thin film metal.

22. An embolic protection device according to claim 21, wherein the thin film metal comprises a nickel titanium alloy.

23. An embolic protection device according to claim 18, wherein the graft member is constructed of braided wire.

24. An embolic protection device according to claim 18, wherein the guidewire has a tubular portion, and further comprising a plurality of arm members integrally formed in the tubular distal portion in proximity with the graft member, the tubular arm members being biased toward an expanded arm position and normally restrained in a retracted arm position by the catheter body, such that relative movement of the guidewire and catheter body direction causes the arm members to move from the retracted arm position toward the expanded arm position to thereby radially expand the proximal end of the graft member.

25. An embolic protection device according to claim 24, wherein the arm members are constructed of braided wire.

26. An embolic protection device according to claim 18, wherein when the graft member expands during movement from the undeployed state to the deployed state, both the geometry of the openings vary compared to the undeployed state and the size of the openings expand.

27. An embolic protection device according to claim 18, wherein the openings are in the form of longitudinal slots in a thin film metal when the graft member is in the undeployed state.

28. An embolic protection device according to claim 27, wherein when the graft member expands during movement from the undeployed state to the deployed state, both the geometry of the openings vary compared to the undeployed state and the size of the openings expand.

29. An embolic protection device according to claim 1, wherein when the graft member expands during movement from the undeployed state to the deployed state, both the geometry of the openings vary compared to the undeployed state and the size of the openings expand.

30. An embolic protection device according to claim 1, wherein the openings are longitudinal slots formed in a thin film metal when the graft member is in the undeployed state.

31. An embolic protection device according to claim 30, wherein when the graft member expands during movement from the undeployed state to the deployed state, both the geometry of the openings vary compared to the undeployed state and the size of the openings expand.

* * * * *